United States Patent [19]
Ogino et al.

[11] Patent Number: 4,497,629
[45] Date of Patent: Feb. 5, 1985

[54] DENTAL IMPLANT AND METHOD OF MAKING SAME

[75] Inventors: Makoto Ogino; Toshihiko Futami, both of Kawasaki; Michio Kariya, Yokohama; Takeo Ichimura, Tokyo; Takamitsu Fujiu, Tokyo, all of Japan

[73] Assignee: Nippon Kogaku K.K., Tokyo, Japan

[21] Appl. No.: 449,426

[22] Filed: Dec. 13, 1982

[30] Foreign Application Priority Data

Jan. 7, 1982 [JP] Japan ................................ 57-1198

[51] Int. Cl.$^3$ .............................................. A61C 8/00
[52] U.S. Cl. ..................................... 433/201; 433/173
[58] Field of Search ................... 433/201, 173; 3/1.9, 3/1.91; 128/92 C

[56] References Cited

U.S. PATENT DOCUMENTS

| | | | |
|---|---|---|---|
| 3,368,712 | 2/1968 | Sanford et al. | 501/10 |
| 3,922,155 | 11/1975 | Broemer et al. | 433/201 |
| 3,987,499 | 10/1976 | Scharbach et al. | 3/1.9 |
| 4,159,358 | 0/1979 | Hench et al. | 427/318 |
| 4,223,412 | 9/1980 | Aoyagi et al. | 433/201 |
| 4,234,972 | 0/1980 | Hench et al. | 3/1.9 |
| 4,365,356 | 12/1982 | Broemer et al. | 3/1.9 |
| 4,411,624 | 10/1983 | Ogino et al. | 433/201 |

Primary Examiner—John J. Wilson
Attorney, Agent, or Firm—Shapiro and Shapiro

[57] ABSTRACT

A dental implant and a method of making same are disclosed. The dental implant comprises a biocompatible metal core and a multi-layer bioglass coating applied on the core. The outer layer of the multi-layer coating is formed of a bioglass whose chemical composition is selected from within the range of composition particularly defined by the present invention and which has substantially the same thermal expansion coefficient as the core. The inner layer is formed of a bioglass whose chemical composition is substantially the same as the glass of the outer layer with the exception that the content of $TiO_2$ is increased within a particularly determined range.

4 Claims, 3 Drawing Figures

DENTAL IMPLANT AND METHOD OF MAKING SAME

BACKGROUND OF THE INVENTION

1. Field of the Invention

The present invention relates to a dental implant comprising a metal core and a layer of biologically active glass or glass ceramics covering the metal core, and also to a method of making the dental implant.

2. Description of the Prior Art

In dental prosthesis many attempts have been made to use a dental root generally called dental implant. When an artificial tooth is to be set for a decayed-out natural tooth, the implant is implanted in the alveolar bone and a dental crown is mounted on the implant. Although this method is very attractive, the conventional dental implants have an important problem. Because of the mechanical strength required for such dental implants they have to be made from those materials which have high mechanical strength such as metal. The bonding between the implant and the bone relies upon the mechanical bonding force (interlocking or anchoring) only. Relying on mere mechanical bonding force it has not always been possible to perfectly fix the implant in the bone. Due to such insufficient stabilization, there has been often caused inflammation in the alveolar bone after implanting. In a relatively short time of use the implant falls out. Because of these drawbacks it has been difficult to put such metal implants to practical use.

Recently, biologically active glasses or glass ceramics have been developed in the art which can directly and chemically combine with bones (cf. Japanese Patent Application laid-open No. 145,394/1978 the counterpart of which is U.S. Pat. Nos. 4,159,358 and 4,234,972). Such biologically active glass or glass ceramics is hereinafter referred to as bioglass. As an application of the bioglass it has been proposed also to make dental implants by covering a metal core with a bioglass layer.

The mechanism of the chemical bonding between bioglass and bone has not yet been fully explained. They say that under the action of body fluids or humor the atoms in the bioglass are dissolved out as ions which deposit in the area near the boundary between bioglass and bone and in some cases there are formed the same compounds as the inorganic compounds in the bone thereby forming a direct and strong bioglass-to-bone bond.

However, it has been found that the properties of the bioglass surface change gradually with the dissolution of ions whereby a layer is formed which has different properties from those of the initial bioglass. The layer may be called a reaction layer. We, the inventors of the present invention have made a vast study on the bioglass and the bonding strength of the bioglass and bone. The study has led us to the following findings:

The forming speed of the above mentioned reaction layer decreases as the bonding between the bioglass and the bone is nearing completion. However, if the reactivity of the bioglass is high, the dissolution of ions from the bioglass steadily continues for a long time although the rate of dissolution becomes lower and the reaction layer continues growing. At last the reaction layer develops up to the interface area between the metal core and the bioglass layer. In general, the reaction layer thus formed is, unfortunately, fragile. The mechanical strength is lower than the original bioglass and, as a matter of course, lower than that of the metal core. Therefore, when the reaction layer has grown too much and in particular when the reaction layer has developed up to the interface area between the bioglass and the core, the bonding strength between the glass and the metal core is reduced markedly. In the worst case, the implant falls out by occlusal pressure.

The above findings lead us to the conclusion that the growth of the reaction layer should be stopped before the reaction layer has developed into the interface area between bioglass and metal core and that the growth of the reaction layer should be stopped preferably in a gentle and gradual manner but not abruptly. An ideal bioglass to satisfy the desire is such glass which has high reactivity at the area near the interface between the glass and the alveolar bone to provide good bondability (good initial bondability) but has low or substantially no reactivity at the area near the interface between the glass and the core to provide good long-term bondability. However, as will be readily understood, a single kind of glass can not satisfy both of the initial bondability and the long-term bondability at the same time. To solve the problem, we have conceived a two-layer bioglass covering comprising an outer layer of high reactivity and an inner layer of low or substantially no reactivity.

The conception of the use of a multi-layer bioglass covering in dental implant is not novel per se. From the description made in the above-referred U.S. Pat. No. 4,159,358 we have been informed of the fact that the prosthetic device disclosed in German Pat. No. DT 2,326,100 B2 has been invented based on a conception similar to our conception of multi-layer bioglass covering described above. The prosthetic device disclosed in the German patent has an intermediate layer formed of less active glass and interposed between a metal core and a bioglass layer.

Generally, the simplest process for covering a metal core with glass is the melt immersion process. However, when this melt immersion process is employed, it is required that the metal core and glass should have the same thermal expansion coefficient. Therefore, if a metal core is immersed in molten glass having different thermal expansion coefficients from that of the metal core, then a serious problem is caused thereby. The glass coating layer formed on the metal core after it is removed from the immersion bath and allowed it to cool down to the room temperature has a large residual stress therein. Due to the large residual stress, the glass breaks or at least the glass is easily broken.

In the above-referred U.S. Pat. No. 4,159,358, Hench et al have proposed the following bioglass composition:

| | |
|---|---|
| $SiO_2$ | 40–60% (by weight) |
| $Na_2O$ | 10–32% |
| CaO | 10–32% |
| $P_2O_5$ | 0–12% |
| $CaF_2$ | 0–18% |
| $B_2O_3$ | 0–20% |

Within the above range of composition such a particular bioglass may be obtained which has the same thermal expansion coefficient as that of a selected biocompatible metal core, for example, that of a cobalt-chromium alloy, SUS 316 stainless steel. However, when such a particular bioglass composition is selected from the above, the biological activity of the glass is directly and exclusively determined by it. Therefore, as stated by Hench et al themselves, it was impossible to obtain implants having different biological activities employing the same metal core. In other words, when one attempts to coat a metal core with two glass layers having different biological activities, one can not select such a combination of two kinds of glass from the glass compositions proposed by Hench et al which are different from each other in activity but the same in thermal expansion coefficient.

For the reason described above, Hench et al gave up the attempt to match the thermal expansion coefficient of bioglass with that of metal core. Instead, they have invented a novel method of making implant (U.S. Pat. No. 4,159,358) which provides the above-mentioned type of implant even when the metal core and the bioglass then used have different thermal expansion coefficients.

However, there are some difficulties in manufacturing a dental implant according to the method proposed by Hench et al.

The metal core generally used in dental implants is very small in size. It is a conical metal member of 3-6 mm in diameter and 8-12 mm in length. Naturally its thermal conductivity is very high. The metal core is immersed in a molten glass mass of high temperature in the range of from 1250° to 1550° C. The essential thing for this process is to rapidly lower the temperature of the molten glass coating layer to a certain critical temperature (Ts) before the temperature of the metal core rises. The critical temperature (Ts) is the temperature at which the temperature dependence of the volume of bioglass becomes non-linear (refer to the patent specification of Hench et al). However, considering the very small size and very high thermal conductivity it is obvious that such rapid cooling is extremely difficult to realize. Generally speaking, a simpler manufacturing process is advantageous from the standpoint of manufacturing cost.

As previously noted, the melt immersion process is the simpliest process for coating a metal core with glass. However, in the case wherein a metal member is to be covered with two layers, an inner glass layer and an outer glass layer, the two glass layers are required to have the same thermal expansion coefficient. Otherwise, the two-layer glass coating formed on the metal core has a large amount of residual stress therein after cooling. Due to the residual stress, the glass coating breaks at once or is easily broken.

Furthermore, the glass for the inner layer is required to have a higher melting point than that for the outer layer. Otherwise, the inner layer melts and flows when the outer layer is applied on it, which results in deformation of the coating.

SUMMARY OF THE INVENTION

Accordingly it is a first object of the invention to provide a dental implant comprising a metal core and at least two bioglass coating layers in which the outer layer which is in contact with alveolar bone after implanted, is composed of a glass having higher biological activity and the inner layer in contact with the metal core is composed of another glass having lower or substantially no biological activity.

It is a second object of the invention to provide a dental implant in which the outer and inner glass coating layers and the metal core have substantially the same thermal expansion coefficient and therefore which can be made employing the melt immersion process.

It is a third object of the invention to provide a dental implant in which the inner layer glass has a melting point higher than that of the outer layer glass and therefore which can be made employing the melt immersion process.

Generally speaking, the bonding strength between two glass layers decreases with the difference in composition between the two layers.

Therefore, it is a fourth object of the invention to provide a dental implant covered with a multi-layer coating in which the composition of the inner layer glass and the composition of the outer layer glass are similar to each other.

The present invention is based on the finding that the following composition of glass can provide very useful bioglass for dental implant although the composition partly corresponds to the composition proposed by Hench et al.

| | |
|---|---|
| $SiO_2$ | 35-60 (mol %) |
| $B_2O_3$ | 0-15 |
| $Na_2O$ | 10-30 |
| $CaO$ | 5-40 |
| $TiO_2$ | 0-2 |
| $P_2O_5$ | 0-15 |
| $K_2O$ | 0-20 |
| $Li_2O$ | 0-10 |
| $MgO$ | 0-5 |
| $La_2O_3 + Ta_2O_5 + Y_2O_3$ | 0-8 |
| $F_2$ | 0-15 |

The glass of the above composition exhibits high biological activity and therefore becomes fixed to bone well and rapidly. The bonding strength between the glass and the bone is high. Furthermore there is provided a glass which has substantially the same thermal expansion coefficient as that of a biocompatible metal core.

The present invention is also based on the following findings:

By adding to a first glass composition selected from within the above composition range a sufficient amount of $TiO_2$ to increase the content of $TiO_2$ to 5-10 mol% there is obtained a second glass composition which is featured by:

① the thermal expansion coefficient (calculated from the volumes measured at 100° C. and 300° C.) substantially equal to the first composition while only the biological activity is reduced as compared with the first composition to such an extent to prevent the above-mentioned overdevelopment of the reaction layer up to the area of the core; and ② the melting point is 30°-50° C. higher than the first composition.

Based on the above findings the present invention provides a dental implant comprising a biocompatible metal core and a multi-layer glass coating applied on said core, said dental implant being characterized in that the outer glass layer is formed of a biologically active glass comprising:

| | |
|---|---|
| $SiO_2$ | 35-60 (mol %) |
| $B_2O_3$ | 0-15 |
| $Na_2O$ | 10-30 |
| $CaO$ | 5-40 |
| $TiO_2$ | 0-2 |
| $P_2O_5$ | 0-15 |

-continued

| | |
|---|---|
| $K_2O$ | 0–20 |
| $Li_2O$ | 0–10 |
| $MgO$ | 0–5 |
| $La_2O_3 + Ta_2O_5 + Y_2O_3$ | 0–8 |
| $F_2$ | 0–15 | and having a thermal expansion coefficient substantially equal to the core, and that the inner glass layer is formed of a glass as obtained by merely adding to said outer layer glass an amount of $TiO_2$ sufficient to increase the content of $TiO_2$ up to 5–10 mol%.

The biocompatible metal core used in the invention may be of, for example, cobalt-chromium alloy, nickel-chromium alloy, iron-base austenite alloy such as stainless steel, etc. Naturally the core should have a mechanical strength equal to or higher than the natural tooth. The above-referred cores have a sufficient mechanical strength for this purpose.

The shape of the core may be suitably selected according to the location of the tooth for which the implant is intended to use. For example, the core may be of a form similar to an inverted cone, inverted truncated cone or inverted truncated quadra-pyramid. However, it is preferred that as a whole the core be of rotation-symmetrical body with its top end being rounded and the tangential line at the top end being perpendicular to the center axis of the core. This preferred shape of the core prevent the local concentration of stress in the bone when a strong external force is applied to the implant. If stress is locally concentrated on the bone, there may be caused troubles such as inflammation and resorption of bone. The preferred shape serves to disperse the stress uniformly in all directions thereby preventing the glass coating from being broken by external force.

After the dental implant has once been implanted in an alveolar bone, the outer glass layer remains in contact with the bone. The outer layer is formed of a bioglass the chemical composition of which has been defined above. Among the components defined above, $TiO_2$ is a component to control the reactivity of the bioglass. $TiO_2$ component depresses the reactivity. $TiO_2$ more than 2 mol% depresses the reactivity too much so that the initial fixability of the implant as wel as the bonding strength between bone and bioglass become poor. $B_2O_3$, $Na_2O$ and CaO are basic components of the bioglass. These components also have an effect on the reactivity of the glass although the effect is very small as compared with $TiO_2$. The reactivity increases with increasing the content of these basic components. Therefore, when the content of these component is extremely high, the glass becomes over-reactive. In this case, there is formed a fragile reaction layer by which the bonding strength is decreased. However, when the content of these components is unduly low, the desired reactivity is lost. Considering these factors, 15 mol% is determined as the upper limit of the content of $B_2O_3$. For $Na_2O$ the upper limit is 30 mol% and the lower limit is 10 mol%. For CaO the upper limit is 40% and the lower limit is 5 mol%.

$SiO_2$ is a network-former. The use of more than 60% $SiO_2$ renders it impossible to attain the desired low melting point. The use of less than 35 mol% $SiO_2$ provides an over-reactive glass the reactivity of which can not be controlled even by $TiO_2$. Such an over-reactivity is unsuitable for purpose of the invention.

$K_2O$ and $Li_2O$ have a similar effect to $Na_2O$ to control the reactivity and to attain lower melting point. Therefore, these two components may be used to replace a part of the content of $Na_2O$. However, when content of $Li_2O$ is over 10 mol%, it is impossible to obtain the biocompatibility.

MgO may be used to replace a part of the content of CaO. However, the use of more than 5 mol% MgO is undesirable in view of the biocompatibility. $F_2$ may be added as an aid in lowering the melting point of the glass. However, with a higher content of $F_2$ than 15 mol% there can not be obtained any suitable reactivity. The content of $La_2O_3$, $Ta_2O_5$ and $Y_2O_3$ in total should be less than 8 mol%. Otherwise, the glass becomes undesirably high in melting point. More than 15 mol% $P_2O_5$ renders it impossible to attain the desired reactivity.

The glass composition for the inner layer corresponds to the above glass composition for the outer layer with the exception that the content of $TiO_2$ is increased to 5–10 mol%. By increasing the content of $TiO_2$ in the second glass composition within the limit defined according to the invention, the reactivity can be reduced as desired without changing the thermal expansion coefficient substantially. With the content of $TiO_2$ within the defined range, the growth of the reaction layer is gradually stopped before it reaches the interface area between the inner layer and the core. Good bonding between the implant and the alveolar bone is maintained for a long time.

In the above, it was said that the thermal expansion coefficient is not changed substantially by the addition of an additional amount of $TiO_2$. This means that the difference in thermal coefficient between the outer and inner glass layers is within the range of $\pm 0.05 \times 10^{-5}$ $°C.^{-1}$. In the area near the interface between the inner and outer glass layers there takes place a counter diffusion of the glass components thereby forming a boundary layer having a substantial width. Since the difference in thermal expansion coefficient between the outer and inner glass layers is very small as noted above, any stress as generated by such a small difference in thermal expansion coefficient will be sufficiently absorbed in the boundary layer.

If desired, an intermediate layer may be interposed between the outer and inner layers within the scope of the present invention. In this case, the intermediate layer is formed of glass as obtained by adding to the glass for the outer layer a less amount of $TiO_2$ than that added to the glass for the inner layer. For example, the contents of $TiO_2$ in the outer layer, intermediate layer and inner layer may be 0 mol%, and 3 mol% and 7 mol%, respectively.

Suitable range of thickness of the glass coating layer is 100 to 1000 μm for inner layer, 100 to 500 μm for the outer layer and 200 to 1500 μm in total.

In either case of the inner layer and the outer layer, the molten glass mass for coating can be prepared employing the method known in the art of glass. According to the selected composition of the glass the raw materials of the respective components of the glass are mixed together in a determined mixing ratio. The raw materials may be in the forms of oxid, carbonate, nitrate, fluoride, etc. The mixed raw materials are pulverized to form a formulated mixture which is then thrown into a platinum pot in an electric furnace heated up to 1000°–1300° C. After melting and refining, the molten glass mass is stirred thoroughly to homogenize the mixture.

A selected metal core is immersed in the molten glass mass prepared in the manner described above. After removal from the molten glass mass, the metal core coated with the inner layer glass is annealed to form the desired inner layer coating on the core. According to necessity, the coated core is polished and shaped. Thereafter, the coated core is immersed in a molten glass mass prepared for the outer layer coating. After the immersion, the above procedure is repeated to form the desired outer glass layer. In this manner, a dental implant according to the invention is made.

In the process for making a dental implant, the inner layer is heated again when the outer layer is applied. Therefore, the glass used for the inner layer should have substantially the same thermal expansion coefficient as the core. Herein, the words "substantially the same thermal expansion coefficient" mean that the thermal expansion coefficient of the glass may be lower than that of the core by $0.1 \times 10^{-5}$° C.$^{-1}$ at most. It never means a thermal expansion coefficient higher than the core, even a little. Conveniently, within the glass composition range for the inner layer defined above, a glass which has substantially the same thermal expansion coefficient as that of a metal core, in particular that of a preferred metal core, can be selected.

Therefore, the present invention provides also a method of making a dental implant comprising the steps of:

(1) immersing a metal core in a molten mass of glass for the inner layer defined above and having substantially the same thermal expansion coefficient as that of said metal core;

(2) removing said core from the molten glass mass;

(3) cooling the coated core up to the glass transition temperature (Tg) of the coating glass;

(4) maintaining said cooled coated core at the same temperature until the temperature of the glass coating layer becomes equal to that of said core;

(5) annealing said coated core at a rate less than 0.8° C./min.;

(6) polishing and shaping said coated core at the normal temperature according to necessity;

(7) immersing said coating core again in a molten glass mass defined above for forming the outer layer; and (8) treating said coated core in the same manner as in the above steps (2)-(6).

According to the method, the combination of core and glass for the inner layer is so selected as to have substantially the same thermal expansion coefficient. Therefore, at the third step (3) the temperatures of the core and the glass are made equal to each other.

The coated core is maintained at Tg for a while. This step is necessary to obtain correspondence of the temperature of the core with the temperature of the glass coating and also to completely release the glass coating from the stress generated in the glass during cooling. If the coated core is maintained at a higher temperature than Tg at this step, it becomes difficult to keep the shape of the glass coating layer (for example to obtain uniform layer thickness). However, if it is maintained at a lower temperature than Tg, then the glass becomes substantially solid and therefore the glass can not be released from the stress previously produced therein. However, when the temperature is within a range 40° C. lower than Tg, the glass can be released from stress by maintaining it at the temperature for a relatively long time, for example, 1 to 24 hours. Therefore, for purpose of the invention, "maintaining the coated core at the glass transition temperature Tg" means that the coated core has to be maintained at a temperature in the range of from Tg to 40° C. lower temperature than Tg.

After releasing the glass layer from the stress generated therein and equalizing the temperatures of the core and the glass layer by maintaining the coated core at Tg for a while, the coated core is annealed at a rate less than 0.8° C./min. to prevent temperature difference between the core and the glass layer as well as between parts of the glass layer itself.

At temperatures under Tg, the temperature dependence of thermal expansion is approximately linear (it is known that this linear relationship can be represented by thermal expansion coefficients measured at temperatures between 100°-300° C.). In the implant making process according to the invention, as described above, there are used a combination of metal core and coating glass which have substantially the same thermal expansion coefficient. Consequently, a dental implant substantially free of any residual stress in the glass layer can be obtained by annealing the coated core while preventing the generation of temperature difference between the core and the glass layer over the annealing temperature range under Tg. According to the invention, the annealing is carried out at a rate less than 0.8° C./min. to prevent the generation of temperature difference between the core and the glass layer during the annealing. This cooling step according to the invention is distinctly different from the cooling step of the prior art process disclosed in the above-referred U.S. Pat. No. 4,159,358. According to the prior art method, the coated core has to be cooled while keeping a predetermined temperature difference between core and glass layer. Obviously the cooling is difficult to carry out even with very strict temperature control. In contrast to the prior art method, according to the present invention, the annealing is carried out without any temperature difference between core and glass layer. Therefore, the temperature control is very simple and a higher productivity is assured.

Furthermore, the method according to the invention has the advantage that it can provide glass coated dental implants having no cracks in the glass layer and being stable against cracking.

In particular, since the inner coating glass and the outer coating glass used in the manufacturing process according to the invention have substantially the same thermal expansion coefficient, the temperature control can be carried out very easily even when the outer coating is applied on the inner coating. It serves also to eliminate the generation of cracks in the multi-layer glass coating. Also, the dental implant obtained by the method according to the invention hardly ever cracks.

For coating a metal core with glass employing the melt immersion process it is desirable that the glass should have a melting point as low as possible. The low melting point of the coating glass is desired for the prevention of damage to the metal core, easy and better work, energy saving etc.

The glass composition for the outer layer defined above provides a relatively low melting point (below 1250° C.). Within the range of glass composition defined above, it has been found that the following composition provides preferred glasses for the outer layer having lower melting point (1000°-1100° C.):

| | |
|---|---|
| SiO$_2$ | 35–55 (mol %) |
| B$_2$O$_3$ | 0–15 |
| Na$_2$O | 15–30 |
| CaO | 8–30 |
| P$_2$O$_5$ | 0–8 |
| TiO$_2$ | 0–2 |
| F$_2$ | 5–15 |

BRIEF DESCRIPTION OF THE DRAWINGS

In FIGS. 1 and 2, P$_1$ and P$_2$ are metal cores, A and B are outer glass coating layers and a and b are inner glass coating layers.

DETAILED DESCRIPTION OF THE PREFERRED EMBODIMENTS

The following examples are given to illustrate the present invention.

EXAMPLE 1

Figure 1:
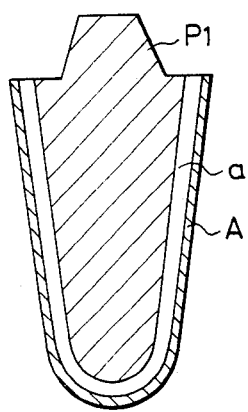
FIG. 1 is a sectional view of a dental implant obtained in Example 1.

FIG. 1 shows a dental implant made in this example.

In FIG. 1, P1 is a metal core made of Co-Cr alloy. The metal core P1 has a shape similar to an inverted cone (5.0 mm in diameter of the upper surface × 11.0 mm in length). The thermal expansion coefficient of the core is $1.43 \times 10^{-5}$ °C.$^{-1}$. A is a bioglass outer layer 200 μm thick and a is a bioglass inner layer 300 μm thick. The chemical compositions of the outer and inner glass layers are shown in Table 1.

TABLE 1

| component | outer layer (A) | inner layer (a) |
|---|---|---|
| SiO$_2$ | 45.9 mol | 4.59 mol |
| B$_2$O$_3$ | 6.3 | 6.3 |
| P$_2$O$_5$ | 2.5 | 2.5 |
| CaO | 21.2 | 21.2 |
| Na$_2$O | 23.6 | 23.6 |
| TiO$_2$ | 0.5 | 5.5 (= 5 mol %) |
| thermal expansion coefficient (°C.$^{-1}$) | $1.36 \times 10^{-5}$ | $1.35 \times 10^{-5}$ |
| Tg (°C.) | 525 | 535 |
| melting point (°C.) | 1250 | 1280 |

The dental implant was made in the following manner:

The metal core was immersed in a molten mass of the glass (a) at 1080° C. After removal from the glass mass, the metal core was allowed to cool. Then, the coated metal core was placed in a constant temperature furnace at 535° C. and held in the furnace for an hour to equalize the temperatures of the core and the glass coating (a). Thereafter it was annealed to room temperature at a rate of 0.5° C./min.

Next, the metal core coated with the inner glass layer (a) was immersed in a molten mass of the glass (A) at 1010° C. After removal from the glass mass, the core was allowed to cool and then introduced into a constant temperature furnace at 525° C. It was held in the furnace for an hour to equalize the temperatures of the core, glass layer (a) and glass layer (A). Thereafter, it was annealed to room temperature at a rate of 0.5° C./min.

The implant of the present invention obtained in the above manner was visually examined. There was observed no crack in the glass coating layers of the implant. Even when the surface of the implant was polished with a diamond grinding stone no crack was produced in the implant.

The dental implant is implanted in an alveolar bone. After the complete bonding between the implant and the bone has been ascertained by checking, an upper structure such as a dental crown is mounted on the implant.

EXAMPLE 2

Figure 2:
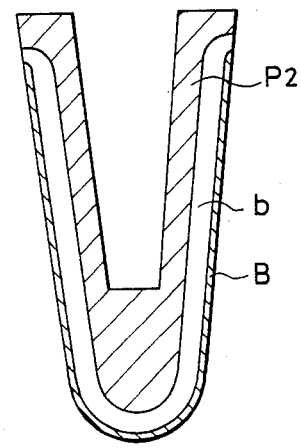
FIG. 2 is a sectional view of a dental implant obtained in Example 2.

FIG. 2 shows a dental implant made in this example.

In FIG. 2, P2 is a metal core formed of a Ni-Cr alloy. The metal core P2 has a shape similar to an inverted cone (4.5 mm in diameter on the upper surface × 10 mm in length) having a recessed portion formed in the upper surface. The thermal expansion coefficient is $1.36 \times 10^{-5}$ °C.$^{-1}$. In use, a post core is fitted in the recessed portion and cemented to it. A dental crown is mounted on the post core or directly mounted on the implant without such a post core.

B is an outer layer bioglass of 100 μm thick. b is an inner layer bioglass of 400 μm thick. The chemical compositions of the outer and inner glass layers are shown in Table 2.

TABLE 2

| component | outer layer (B) | inner layer (b) |
|---|---|---|
| SiO$_2$ | 46.1 mol | 46.1 mol |
| B$_2$O$_3$ | 6.0 | 6.0 |
| P$_2$O$_5$ | 2.7 | 2.7 |
| CaO | 21.0 | 21.0 |
| Na$_2$O | 23.7 | 23.7 |
| TiO$_2$ | 0.5 | 5.5 (= 5 mol %) |
| thermal expansion coefficient (°C.$^{-1}$) | $1.36 \times 10^{-5}$ | $1.36 \times 10^{-5}$ |
| Tg (°C.) | 520 | 530 |
| melting point (°C.) | 1230 | 1280 |

The dental implant was made in the following manner:

The metal core was immersed in a molten mass of the glass (b) at 1070° C. After removal from the molten glass mass, the core was allowed to cool and then placed in a constant temperature furnace at 530° C. It was held in the furnace for an hour to equalize the temperatures of the core and the glass coating layer (b). Thereafter, it was annealed to room temperature at a cooling rate of 0.5° C./min.

Next, the metal core coated with the inner layer glass (b) was immersed in a molten mass of the glass (B) at 1000° C. After removal from the molten glass mass, the core was allowed to cool and then placed in a constant temperature furnace at 520° C. It was held in the furnace for an hour to equalize the temperatures of the core, inner glass layer (b) and outer glass layer (B). Thereafter, it was annealed to room temperature at a rate of 0.5° C./min. Thus, the above shown dental implant was prepared.

The dental implant obtained in the above manner was visually examined. There was observed no crack in the glass coating layers of the implant. The surface of the implant was polished with a diamond grinding machine. No cracks were produced in the implant.

EXAMPLE 3

A dental implant was prepared employing the same metal core as that used in Example 1. The metal core was coated with an inner layer of bioglass 250 μm thick at first and then with an outer layer of bioglass 250 μm thick. The glasses used for forming the inner layer and the outer layer are shown in Table 3.

TABLE 3

| component | outer layer | inner layer |
|---|---|---|
| $SiO_2$ | 47.1 mol | 47.1 mol |
| $B_2O_3$ | 12.1 | 12.1 |
| $P_2O_5$ | 2.8 | 2.8 |
| CaO | 10.0 | 10.0 |
| $Na_2O$ | 24.3 | 24.3 |
| $CaF_2$ | 3.3 | 3.3 |
| $TiO_2$ | 0.4 | 6.0 (= 6 mol %) |
| thermal expansion coefficient (°C.$^{-1}$) | $1.30 \times 10^{-5}$ | $1.29 \times 10^{-5}$ |
| Tg (°C.) | 490 | 490 |
| melting point (°C.) | 1100 | 1150 |

At first, the metal core was immersed in a molten mass of the glass for the inner layer at 980° C. After removal from the molten glass mass, the core was allowed to cool for a while and then placed in a constant temperature furnace to 500° C. It was held in the furnace for an hour to equalize the temperatures of the core and the inner glass coating layer. Thereafter it was annealed to room temperature at a rate of 0.5° C./min.

Next, the metal core coated with the inner glass layer was immersed in a molten mass of the glass for outer layer at 950° C. After removal from the molten glass mass, the core was allowed to cool for a while and then introduced into an annealing furnace at 490° C. It was held in the furnace for an hour to equalize the temperatures of the core, inner glass layer and outer glass layer. Thereafter it was annealed to the room temperature at a rate of 0.5° C./min.

The dental implant of the invention thus prepared was visually examined. No crack was observed in the glass coating layers of the implant. The surface of the implant was polished with a diamond grinding machine. No crack was produced on the implant.

EXAMPLE 4

A metal core formed of an iron-base austenite alloy and having a thermal expansion coefficient of $1.61 \times 10^{-5}$° C.$^{-1}$ was used. The core has the same shape as that of the metal core used in Example 1. Glasses shown in Table 4 were used to form inner and outer glass coating layers.

TABLE 4

| glass layer | outer layer | inner layer |
|---|---|---|
| thickness (μm) | 300 | 200 |
| components | | |
| $SiO_2$ | 46.6 mol | 46.6 mol |
| $P_2O_5$ | 2.6 | 2.6 |
| CaO | 13.8 | 13.8 |
| $CaF_2$ | 13.4 | 13.4 |
| $Na_2O$ | 23.6 | 23.6 |
| $TiO_2$ | 0 | 5.3 (= 5 mol %) |
| thermal expansion efficient (°C.$^{-1}$) | $1.57 \times 10^{-5}$ | $1.53 = 10^{-5}$ |
| Tg (°C.) | 420 | 443 |
| melting point (°C.) | 1050 | 1090 |

The metal core was immersed in a molten mass (890° C.) of the inner layer glass. After removal from the molten mass, the core was allowed to cool and then placed in a constant temperature furnace at 450° C. It was held in the furnace for two hours and then annealed to a room temperature at a rate of 0.5° C./min.

Next, the metal core coated with the inner glass layer was immersed in a molten mass (840° C.) of the outer layer glass. After removal from the molten glass mass, the coated core was allowed to cool for a while and then placed in a constant temperature furnace at 430° C. It was held in the furnace for three hours and then annealed to room temperature at a rate of 0.5° C./min. In this manner, a dental implant of the invention was obtained.

REFERENCE EXAMPLE

Four samples of glass were prepared by varying the content of $TiO_2$ while maintaining the contents of $B_2O_3$, $SiO_2$, $Na_2O$ and CaO almost unchanged as shown in the following table, Table 5. The content of $B_2O_3$ in these four glass samples is relatively high. These four samples were compared with each other regarding thermal expansion coefficient and reactivity.

TABLE 5

| glass composition | (1) | (2) | (3) | (4) | (5) | (6) |
|---|---|---|---|---|---|---|
| $SiO_2$ | 49.5 mol | 49.5 mol | 49.5 mol | 49.5 mol | 49.5 mol | 49.5 mol |
| $B_2O_3$ | 12.0 | 12.0 | 12.0 | 12.0 | 12.0 | 12.0 |
| $Na_2O$ | 23.0 | 23.0 | 23.0 | 23.0 | 23.0 | 23.0 |
| CaO | 15.0 | 15.0 | 15.0 | 15.0 | 15.0 | 15.0 |
| $TiO_2$ | 0.5 | 1.0 | 2.0 | 3.0 | 5.0 | 7.0 |
| $TiO_2$ Content (mol %) | 0.5 | 1 | 2 | 3 | 5 | 7 |
| thermal expansion coefficient ($\times 10^{-5}$ °C.$^{-1}$) | 1.3 | 1.3 | 1.3 | 1.3 | 1.3 | 1.3 |

As seen from the above Table 5, these four bioglass samples have all the same thermal expansion coefficient although they have different contents of $TiO_2$. On the other hand, it is clearly seen from FIG. 3 that the reactivity of bioglass can be successfully changed by changing the content of $TiO_2$.

Figure 3:
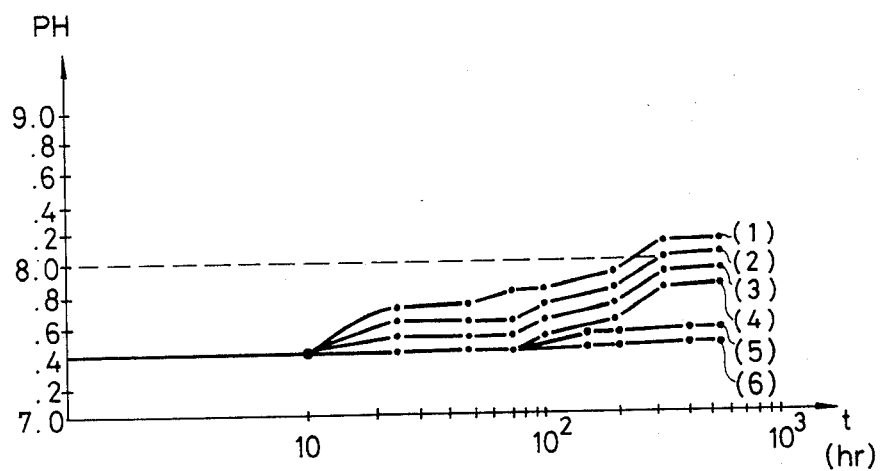
FIG. 3 is a graph showing the change in pH of a pseudo physiological buffer solution observed when four bioglass samples (1)–(6) were being maintained in the solution, the four samples being different from each other in composition.

FIG. 3 is a graph showing the change of pH of a pseudo physiological buffer solution observed when the above bioglass samples (1)-(6) were retained in the solution. The curves (1)-(6) are plotted with pH of the solution as the ordinate and treatment time t (hr.) in logarithm as the abscissa. The graph shows that the highest pH was given by the glass sample (1) having the least content of $TiO_2$ and the lowest pH was given by the sample (6) having the largest content of $TiO_2$. The least rise of pH means the lowest reactivity of bioglass and the largest rise of pH means the highest reactivity. Therefore, the graph demonstrates that the reactivity of bioglass can be controlled as desired by varying the content of $TiO_2$ in the glass.

As readily understood from the foregoing, the present invention provides dental implants having many advantages over the prior art. The dental implant obtained according to the invention exhibits better initial implant-to-bone bondability and good durability. It has no crack in the glass coating layer and substantially no residual stress in the glass coating. Therefore the glass coating hardly ever breaks or cracks. It withstands well any external force as applied by polishing and grinding.

Furthermore, the making method of dental implants according to the invention has the advantages of easy temperature control and very feasible processing steps.

While the invention has been particularly shown and described with reference to preferred embodiments thereof, it will be understood by those skilled in the art that the foregoing and other changes in form and details can be made therein without departing from the spirit and scope of the invention.

We claim:

1. A dental implant comprising a biocompatible metal core and a multi-layer glass coating applied on said core, said dental implant being characterized in that an outer layer of said multi-layer glass coating is formed of a biologically active glass composed of:

| | |
|---|---|
| $SiO_2$ | 35–60 mol % |
| $B_2O_3$ | 0–15 |
| $Na_2O$ | 10–30 |
| CaO | 5–40 |
| $TiO_2$ | 0–2 |
| $P_2O_5$ | 0–15 |
| $K_2O$ | 0–20 |
| $Li_2O$ | 0–10 |
| MgO | 0–5 |
| $La_2O_3 + Ta_2O_5 + Y_2O_3$ | 0–8 |

-continued

| | |
|---|---|
| $F_2$ | 0–15 | and having substantially the same thermal expansion coefficient as that of said metal core, and that an inner layer of said multi-layer glass coating is formed of a lower or substantially no biologically active glass as obtained by merely increasing the content of $TiO_2$ in the glass composition selected for said outer layer to 5–10 mol%.

2. A dental implant according to claim 1, wherein said outer layer is formed of a glass composed of:

| | |
|---|---|
| $SiO_2$ | 35–55 mol % |
| $B_2O_3$ | 0–15 |
| $Na_2O$ | 15–30 |
| CaO | 8–30 |
| $TiO_2$ | 0–2 |
| $P_2O_5$ | 0–8 |
| $F_2$ | 5–15 |

3. A dental implant according to claim 1, wherein said metal core is made of a metal selected from the group consisting of cobalt-chromium alloy, nickel-chromium alloy and iron-base austenite alloy.

4. A dental implant according to claim 1, wherein said inner layer has a thickness in the range of from 100 to 1000 μm and said outer layer has a thickness in the range of from 100 to 500 μm.

* * * * *